United States Patent [19]

Kearney et al.

[11] Patent Number: 5,729,958
[45] Date of Patent: *Mar. 24, 1998

[54] METHOD FOR MANUFACTURING FREEZE DRIED DOSAGES IN A MULTILAMINATE BLISTER PACK

[75] Inventors: Patrick Kearney; Andrew Roy Thompson, both of Swindon; Richard John Yarwood, Nr Swindon, all of Great Britain

[73] Assignee: R. P. Scherer Corporation, Troy, Mich.

[*] Notice: The term of this patent shall not extend beyond the expiration date of Pat. No. 5,343,672.

[21] Appl. No.: 448,469

[22] PCT Filed: Nov. 30, 1993

[86] PCT No.: PCT/GB93/02459

§ 371 Date: Nov. 15, 1995

§ 102(e) Date: Nov. 15, 1995

[87] PCT Pub. No.: WO94/12142

PCT Pub. Date: Jun. 9, 1994

[51] Int. Cl.$^6$ ................................................ B65B 55/14
[52] U.S. Cl. ........................................ 53/440; 53/453
[58] Field of Search ........................... 53/432, 433, 440, 53/454, 453, 461, 514, 127; 206/532, 538, 539, 484

[56] References Cited

U.S. PATENT DOCUMENTS

| 4,305,502 | 12/1981 | Gregory et al. | 53/432 |
| 4,371,080 | 2/1983 | Haines | 206/532 |
| 4,754,597 | 7/1988 | Buxton et al. | 53/432 |
| 5,310,060 | 5/1994 | Bitner et al. | 206/532 |
| 5,343,672 | 9/1994 | Kearney et al. | 53/440 |
| 5,469,968 | 11/1995 | Matthews et al. | 206/532 |

FOREIGN PATENT DOCUMENTS

| 0083323 | 7/1983 | European Pat. Off. | 53/453 |
| 5025879 | 9/1970 | Japan | 53/453 |

*Primary Examiner*—Daniel Moon
*Assistant Examiner*—Ed Tolan
*Attorney, Agent, or Firm*—Nixon & Vanderhye

[57] ABSTRACT

An improved method for manufacturing freeze dried pharmaceutical tablets in blister packs is disclosed. Liquid dosages are introduced into a multilayer laminated blister sheet having an impermeable intermediate layer (14) that is positioned between first and second outer layer (16, 18) each of which has substantially the same coefficient of thermal expansion. The properties of the outer layers of the blister sheet are such that there are no inter-layer stresses that will cause curvature of the blister sheet when it is subjected to temperature changes during the freezing and freeze drying steps. Following the introduction of the dosages into the depressions (10) of the blister sheet, the dosages are frozen and freeze dried. A lidding sheet (32) is then attached to the blister sheet to seal the solid dosages into the blister pack.

1 Claim, 1 Drawing Sheet

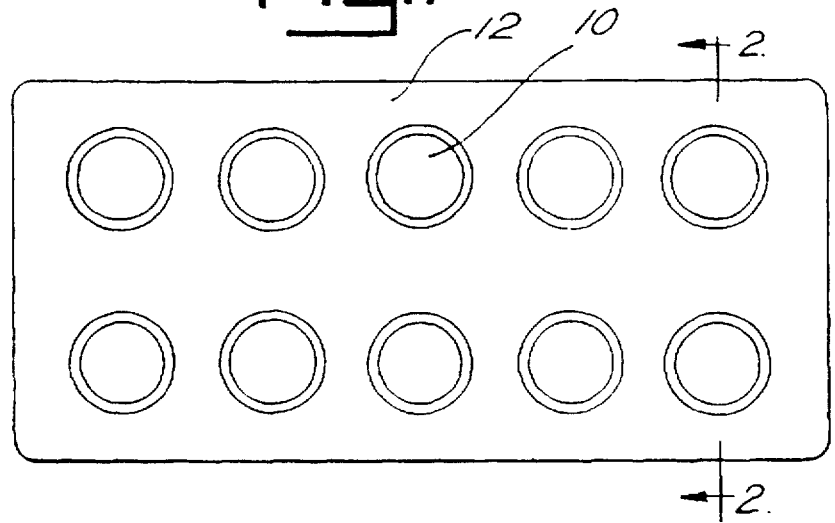
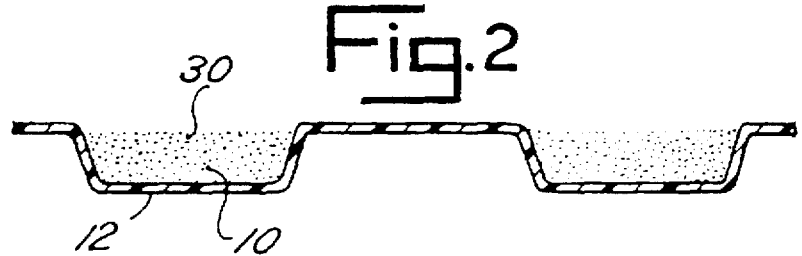
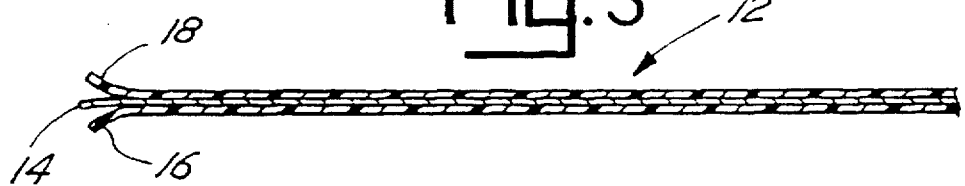
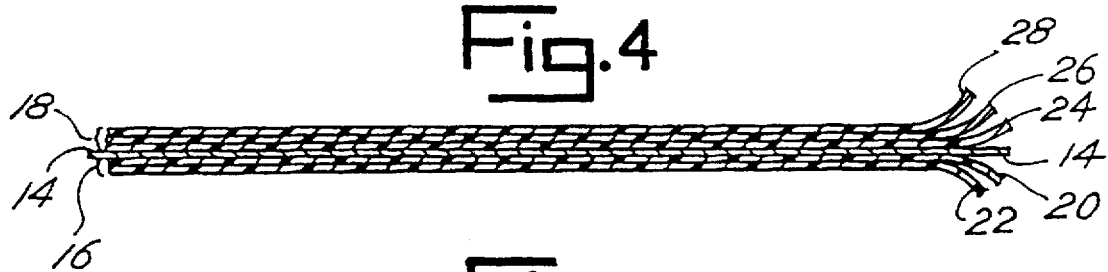
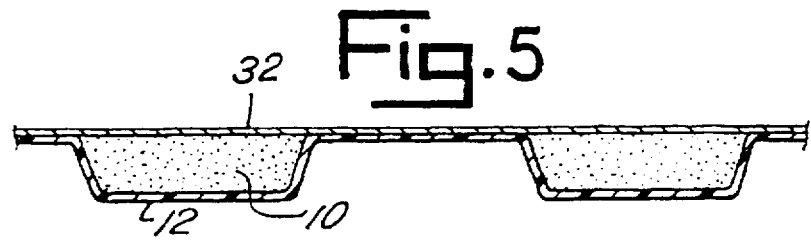

METHOD FOR MANUFACTURING FREEZE DRIED DOSAGES IN A MULTILAMINATE BLISTER PACK

BACKGROUND OF THE INVENTION

This invention relates generally to the field of manufacturing and dispensing pharmaceuticals, and more particularly to an improved method for manufacturing freeze dried pharmaceutical tablets in disposable single dose aluminum blister packs. In recent years, pharmaceutical producers have turned to the use of blister packs for use in both the forming and dispensing of pharmaceutical tablets. These blister packs generally consist of a blister sheet or a blister film and a lidding sheet. The blister sheet contains depressions for containing individual dosages. In a standard process for manufacturing freeze dried tablets, a single dosage, in liquid form, is introduced into each depression of the blister sheet. The blister sheet, along with the liquid dosages, is then placed into a refrigerated environment where the dosages are subjected to low temperatures to freeze them. The blister sheets are then transferred to a freeze drier, where the ice is removed by sublimation. When freeze drying is completed, the sheets are removed from the drying chamber and covered with an adhesive lidding sheet, which seals the solid dosages into their individual depressions. U.S. Pat. No. 4,305,502 is incorporated herein by reference as teaching, inter alia, a known process for manufacturing freeze dried tablets.

However, blister sheets that have heretofore been used in freezing and freeze drying processes have suffered from several deficiencies. First, the blister sheets have typically been made of a polymeric substance, which, over time, can allow moisture to permeate the blister pack and reach the dosages stored inside. To solve this problem, blister sheets have been developed in which a layer of aluminum is laminated between layers of polymer. While the presence of the aluminum layer prevents moisture from permeating the blister pack, it leads to a second problem. Namely, when subjected to temperature changes during the freezing process, conventional aluminum/polymer laminates tend to curl up, due to the differences in the degree of thermal expansion or contraction of the opposing layers of the laminate. This makes their use in freezing processes difficult, since liquid product can easily spill from the formed depressions or can lie unevenly in the depressions during filling and freezing operations. Furthermore, the curling of the blister sheet can cause dosages to freeze or sublimate unevenly, since some depressions may not be in physical contact with the cold surfaces of the refrigerator or freeze drier. The only solution has been to use weights on the edges of the laminate strips to hold them sufficiently flat. Such measures are not practical in large scale manufacturing operations, and can interfere with the freezing process.

A need therefore exists for a method of utilizing a high barrier aluminum laminate in the manufacture of freeze dried dosage forms that avoids the problem of curling of the blister sheet.

SUMMARY OF THE INVENTION

In a basic aspect, the invention is an improved method for manufacturing freeze dried dosage forms in aluminum blister packs. The dosages are introduced as a liquid into the depressions of a blister sheet. The blister sheet comprises an impermeable intermediate layer positioned between first and second outer layers, with each of the outer layers having substantially the same overall coefficient of thermal expansion, as that term is defined herein. The properties of the outer layers of the laminate are such that there are no inter-layer stresses that will cause curvature of the laminate when it is subjected to temperature changes during the freeze drying process. The symmetrical response of the outer layers to such temperature changes can be achieved by using the same film material for both outer layers, or by using different materials which, by virtue of their intrinsic properties or thickness, exhibit similar degrees of thermal expansion or contraction. The outer layers can each consist of separate sublayers, as long as the sublayers in one outer layer are such that the outer layer, as a whole, exhibits the same overall degree of expansion or contraction as the other outer layer. Following the introduction of the dosages into the depressions of the blister sheet, the dosages are frozen and freeze dried. A lidding sheet is then attached to the blister sheet to seal the solid dosages into the blister pack.

BRIEF DESCRIPTION OF THE DRAWINGS

FIG. 1 of the drawing is a plan view of a blister sheet, showing the configuration of the dosage depressions;

FIG. 2 of the drawing is a transverse cross sectional view of said blister pack, taken generally along the line 2—2;

FIG. 3 of the drawing is a cross sectional view of a blister sheet illustrating in further detail the relationship between the intermediate and outer layers of the blister sheet;

FIG. 4 of the drawing is a cross sectional view of a blister sheet illustrating in further detail the relationship between the various layers and sublayers of the blister sheet;

FIG. 5 of the drawing is a cross sectional view of a blister pack with the lidding sheet in place.

DETAILED DESCRIPTION OF THE PREFERRED EMBODIMENTS

As discussed above, the invention is an improved method for manufacturing freeze dried dosage forms in aluminum blister laminates. Turning to FIG. 1 and FIG. 2, to form the blister pack, depressions 10 are formed in a strip 12 of the desired laminate through conventional cold forming. The size and shape of the depressions is a mater of choice that will be dictated by the size and nature of the tablet to be formed, as well as other considerations that are well known to those persons skilled in the art.

Turning to FIG. 3, the laminate strip 12 comprises an intermediate layer 14 that is substantially impermeable to moisture. The preferred material for the intermediate layer is aluminum having a thickness of 10 to 100 µm, with the preferred thickness being approximately 45 µm, although other suitable materials may be used in its place. The intermediate aluminum layer 14 is sandwiched between a first outer layer 16 and a second outer layer 18. The outer layers may be coated or laminated onto the intermediate layer, but the layers do not necessarily have to be bonded together. The first and second outer layers are preferably made of polymeric substances, including polyamide, polyvinylchloride, polypropylene or other such substances. The first and second outer layers can be made of the same or different materials, and may have different thicknesses, as long as they have substantially similar coefficients of thermal expansion, i.e., are made of such materials and have such thickness that the first and second outer layers exhibit substantially the same degree of expansion or contraction within the plane of the film when the laminate is subjected to changes in temperature, particularly within the range of temperatures encountered during the freezing process, in which temperatures can be as low as −196° C. For instance, the laminated film 12 can consist of an intermediate layer 14 of aluminum, positioned between first and second outer layers of polypropylene 16 and 18, each layer being approximately 50 μm thick.

Turning to FIG. 4, it can be seen that one or both of the outer layers can also consist of separate sublayers, with each sublayer being either polymeric or nonpolymeric. For instance, the first outer layer 16 can consist of two or more sublayers, such as a polyamide sublayer 20 and a polyvinylchloride sublayer 22. The second outer layer 18 can consist of a identical sublayers, or can also consist of two or more sublayers, illustrated as 24, 26 and 28, that are different than the sublayers in the first outer layer 16. Materials that may be used as sublayers include the above mentioned polymers, as well as lacquer, aluminum or paper. A priming layer can also be included. Again, the primary concern is that the first outer layer 16 and the second outer layer 18 exhibit, overall, substantially the same degree of expansion or contraction in response to temperature changes, so as to prevent curling of the blister sheet.

Returning to FIG. 1, a single dosage 30 of pharmaceutical, in liquid form, is introduced into each depression in the blister sheet in a conventional manner. The blister sheet is then placed into a refrigeration unit, for instance a nitrogen spray freezing chamber, where both the sheet and the dosages are subjected to temperatures sufficient to rapidly freeze the dosages, typically as low as −196° C. Once the dosages have frozen, the blister sheet is transferred to a freeze drying chamber. Within the freeze drying chamber, the dosages are subjected to a vacuum of typically 0.1 to 1.0 mBar for a period of 180 to 500 minutes. At the same time, the temperature is steadily increased from typically about −30° C. to about 60° C. As shown in FIG. 5, once the dosages have been freeze dried, an adhesive lidding sheet 32 is positioned over the blister sheet, sealing the dosages into the individual depressions of the blister sheet. The procedures associated with the introduction of dosages into the blister sheet, the freezing and freeze drying of the dosages and the attachment of the lidding sheet are known to persons of skill in the art, and need not be treated in great depth herein.

While in the foregoing there have been described preferred embodiments of the invention, it should be understood to those skilled in the art that various modifications and changes can be made without departing from the true spirit and scope of the invention.

What is claimed is:

1. A method for packaging a dosage formed from a liquid comprising the steps of:

(a) forming a first polymeric sheet;

(b) forming a second polymeric sheet having substantially the same coefficient of thermal expansion as the first polymeric sheet;

(c) forming an aluminum sheet;

(d) sandwiching said aluminum sheet between said first and second polymeric sheets to form a multilayer blister film defining a film plane, the multilayer blister film providing a substantially thermally balanced laminate;

(e) forming a plurality of depressions in said multilayer blister film;

(f) introducing the liquid into said depressions;

(g) freezing the liquid, the thermally balanced laminate substantially avoiding warpage of the film plane interposed between the depressions; and (h) attaching a lidding sheet to the multilayer blister film to seal the depressions thereof.

* * * * *